United States Patent [19]
Blackburn et al.

[11] Patent Number: 5,804,549
[45] Date of Patent: Sep. 8, 1998

[54] COMPOSITIONS WITH ACTIVITY AGAINST HELICOBACTER

[75] Inventors: Peter Blackburn, New York; Beth P. Goldstein, Tarrytown; Debra J. Cook, New York, all of N.Y.

[73] Assignee: AMBI Inc., Tarrytown, N.Y.

[21] Appl. No.: 770,521

[22] Filed: Dec. 20, 1996

Related U.S. Application Data

[60] Provisional application No. 60/009,872 Jan. 5, 1996.

[51] Int. Cl.⁶ .......................... A61K 38/00; A61K 31/22
[52] U.S. Cl. .................................. 514/2; 514/12; 514/546
[58] Field of Search .................................. 514/2, 12, 546

[56] References Cited

U.S. PATENT DOCUMENTS

| | | | |
|---|---|---|---|
| 4,485,029 | 11/1984 | Kato et al. | 252/106 |
| 4,980,163 | 12/1990 | Blackburn et al. | 424/94.63 |
| 5,135,910 | 8/1992 | Blackburn et al. | 514/2 |
| 5,217,950 | 6/1993 | Blackburn et al. | 514/2 |
| 5,260,271 | 11/1993 | Blackburn et al. | 514/2 |
| 5,304,540 | 4/1994 | Blackburn et al. | 514/2 |
| 5,328,846 | 7/1994 | Wedler | 435/264 |

FOREIGN PATENT DOCUMENTS

| | | |
|---|---|---|
| WO9218111 | 10/1992 | WIPO . |
| WO9218143 | 10/1992 | WIPO . |
| WO9409806 | 5/1994 | WIPO . |

OTHER PUBLICATIONS

Petschow, et al., Gastroenterology 108, p. A191 (1995).
Seppälä, et al., Annuals of Medicine 27, pp. 601–604 (1995).

*Primary Examiner*—Kevin E. Weddington
*Attorney, Agent, or Firm*—White & Case L.L.P.

[57] ABSTRACT

Disclosed are compositions of nisin and GML as active ingredients for the killing of Helicobacter, as well as methods for eradicating Helicobacter colonization and treatment of Helicobacter infection which employ the GML/nisin compositions.

11 Claims, 1 Drawing Sheet

COMPOSITIONS WITH ACTIVITY AGAINST HELICOBACTER

CROSS-REFERENCE TO RELATED APPLICATIONS

This application claims the benefit, under 35 U.S.C. § 119(e), of U.S. Provisional Pat. application No. 60/009,872, filed on Jan. 5, 1996.

TECHNICAL FIELD OF THE INVENTION

The invention concerns compositions consisting essentially of the lanthionine containing bacteriocin, nisin in combination with glycerol monolaurate and the use of such composition, for the treatment of bacterial infections of the genus Helicobacter.

BACKGROUND AND SUMMARY OF THE INVENTION

Much of the scientific literature relating to the antimicrobial activities of either GML or nisin deal with their activity against Gram-positive bacteria and their inactivity against Gram-negative bacteria in the absence of a chelator or other potentiating agent.

Glycerol monolaurate (GML), also called monolaurin, is the lauryl ester of glycerol. It is used as a surfactant, preservative and refatting agent in cosmetics and cosmetic cleansers and has found limited use as a food preservative.

GML has been recognized as safe by the FDA. Chapter 21, Part 184 of the Code of Federal Regulations (CFR) includes monoglycerides among those compounds affirmed as GRAS (generally recognized as safe). Section 184.1505 of 21 CFR states further that monoglycerides, including GML, meet the specifications of the Food Chemicals Codex and can be used in food with no limitation other than current good manufacturing practice.

GML and other naturally occurring or synthetic monoglycerides, containing saturated or unsaturated fatty acids, have activity against Gram-positive bacteria [Kabara, J. J., 1986. Dietary lipids as anticariogenic agents. J. Environ. Pathol. Toxicol. Oncol. 6:87–113], but are generally considered to be inactive against Gram-negative bacteria [Schlievert, et al. 1992. Effect of glycerol monolaurate on bacterial growth and toxin production. Antimicrob. Ag. Chemother. 36:626–631.]

Fatty acid esters of other polyhydric alcohols, such as sugars, have also been reported to have antimicrobial activity against Gram-positive bacteria. [Conley, A. J. & J. J. Kabara, 1973. Antimicrobial action of esters of polyhydric alcohols. Antimicrob. Ag. Chemother. 4:501–506].

In the presence of potentiators such as chelators, some of these compounds, including GML, have been reported to have inhibitory activity against some common species of Gram-negative bacteria, such as *Escherichia coli* and other Enterobacteriaceae and *Pseudomonas aeruginosa,* which are not affected by the esters in the absence of potentiating agents. [Shibasaki, I. & N. Kato, 1978. Combined effects on antibacterial activity of fatty acids and their esters against Gram-negative bacteria. In Kabara, J. J., ed. Symposium on the Pharmacological Effect of Lipids. The American Oil Chemists' Society Champaign, Illinois, pp 15–24.] The same authors have reported bactericidal activity of GML, in the presence of citrate as chelator, against Escherichia coli, incubated in water.

U.S. Pat. No. 4,485,029 to Kato et al. discloses the use of glycerol monolaurate in combination with one or more antimicrobial agents such as esters of para-hydroxy-benzoic acid and, optionally an organic surfactant in compositions useful in cleaning, disinfecting and preserving contact lenses. Kato et al. do not disclose that GML compositions could be useful in treating infection by Gram-negative bacteria or that GML can be used in combination with a lanthionine-containing bacteriocin such as nisin.

The use of GML as an antimicrobial agent without potentiating agents, against Gram-negative pathogens whose primary hosts are mammals, has not been previously demonstrated. GML is highly lipophilic and poorly soluble in water. For this reason, studies of its antimicrobial activity have generally necessitated the use of concentrations of ethanol that are unacceptable for some pharmacological applications.

Nisin is a polypeptide with antimicrobial properties and is produced in nature by various strains of the bacterium *Lactococcus (Streptococcus) lactis.* Nisin is used as a food preservative for inhibiting bacterial growth and the outgrowth of spores of certain species of Gram-positive bacilli. Nisin is found naturally-occurring in low concentrations in milk and cheese, and is believed to be completely non-toxic and non-allergenic to humans.

Nisin has been recognized as safe by the FDA as a direct food ingredient in pasteurized cheese spread, pasteurized processed cheese spread, and pasteurized or pasteurized processed cheese spread with fruits, vegetables, or meats. Since it is a polypeptide, any nisin residues remaining in foods are quickly digested once they pass into the small intestine.

Although the prior art taught that nisin is ineffective against Gram-negative bacteria and is effective against only a very limited group of Gram-positive bacteria, compositions comprising nisin, particularly in combination with various non-bactericidal agents, have since been shown to be highly active against various species of Gram-positive and Gram-negative bacteria (U.S. Pat. Nos. 5,135,910; 5,217,950 and 5,260,271). More recently, bactericidal activity of nisin, in the presence of chelators, has been described against additional Gram-negative bacteria, including *Helicobacter pylori* (U.S. Pat. Nos. 5,304,540 and 5,334,582).

Coassigned U.S. Pat. Nos. 4,980,163; 5,135,910; 5,217,950; 5,260,271; 5,334,582 and 5,304,540 disclose surfactants, including glycerides as enhancers of the bactericidal activity of lanthionine-containing bacteriocins. For example, U.S. Pat. Nos. 5,135,910; 5,217,950 and 5,260,271 disclose that monolaurin or monooleate in combination with a lanthionine-containing bacteriocin such as nisin is effective in killing the Gram-positive bacterial species *Streptococcus agalactiae* and *Listeria monocytogenes.* U.S. Pat. No. 4,980,163 discloses that a monoglyceride in combination with lysostaphin, a lanthionine-containing bacteriocin such as nisin and the chelating agent EDTA, enhances the bactericidal activity of the composition against *Staphylococcus aureus* and *Streptococcus agalactiae.* There is no suggestion in U.S. Pat. Nos. 4,980,163; 5,135,910; 5,217,950 and 5,260,271 that nisin and glyceride compositions would be active against Gram-negative bacteria, such as Helicobacter.

Many gastrointestinal pathogens are Gram-negative bacteria. In view of the teachings of the prior art, one would expect that GML or surfactants alone would be inactive against such organisms. An example of such a pathogen is *Helicobacter pylori* (also identified in the prior art as *Campylobacter pylori*), a Gram-negative microaerophilic bacillus that colonizes the gastric mucosa. It is a very unusual organism, because it grows in the inhospitable, acidic environment of the human stomach [Hazell, et al., 1986. *Campylobacter pyloris* and gastritis: association with intracellular spaces and adaptation to an environment of mucus as important factors in colonization of the gastric epithelium. J. Infect. Dis. 153: 658–663]. Other species of Helicobacter infect the stomachs of various mammals.

It is now well established that *Helicobacter pylori* is implicated in the pathogenesis of various gastrointestinal diseases, including, gastritis, ulcer and certain gastrointestinal cancers, a finding that has revolutionized the approach to treating these common disorders [Marshall, 1988. The *Campylobacter pylori* story. Scand. J. Gastroenterol. 146 (Suppl.): 58–66; Glise, 1990. Epidemiology in peptic ulcer disease. Current status and future aspects. Scand. J. Gastroenterol. 25: 13–18; Clarkson, et al., 1993. Gastric cancer and *Helicobacter pylori* infection. J. Clin. Pathol. 46: 997–999; Yamada, et al., 1994. *Helicobacter pylori* peptic ulcer disease. JAMA 272: 65–69]. Helicobacter colonization has also been implicated in predisposing individuals to coronary disease and stroke.

Although *H. pylori* is susceptible to a number of antimicrobial agents, monotherapies have not as yet proven to be clinically effective. Moreover, strains resistant to two of the antimicrobial agents, metronidazole and clarithromycin, have already emerged [Boron, et al., 1994. *Helicobacter pylori* binds to blood group antigens. Scientific Amer. Science & Med. 1:28–37]. The currently preferred treatment of gastric ulcer involves therapy with three different antimicrobial agents, some of which may be poorly tolerated [Marshall, 1993. Treatment strategies for *Helicobacter pylori* infection. Gastroenterol. Clin. North Am. 22:183–198]. None of the regimens is completely effective in achieving eradication of *H. pylori,* and many patients fail to complete a course of therapy due to poor tolerability of the regimens [Bell, et al., 1993. *Helicobacter pylori* eradication: efficacy and side effect profile of a combination of omeprazole, amoxycillin and metronidazole compared with four alternative regimens. Quart. J. Med. 86:743–750]. Therefore new agents are needed. It is possible that this disease state will never yield to a single antibacterial agent, and therefore, it may be necessary to combine new treatments with existing or other, new agents, in order to achieve reliable, long-term eradication with good tolerability and compliance.

We have found that concentrations of GML and of nisin that alone are suboptimal in their bactericidal effect, mutually enhance the bactericidal activity of one another in combination against strains of the genus Helicobacter. Although nisin, when tested in the absence of GML, requires the presence of potentiating agents such as chelators to exert effective bactericidal activity against *Helicobacter pylori* and against most other Gram-negative bacteria, the mutually synergistic effect of nisin with GML does not require the presence of chelators or of other potentiating nonbactericidal agents. Therefore, the strong synergistic effect of nisin, in the absence of chelator, with low concentrations of GML against *H. pylori* is surprising.

Helicobacter and other gastrointestinal bacteria reside in the environment of the mucosa. Mucus is a viscoelastic layer secreted by mucosal epithelia and forms a protective barrier between the epithelium and its immediate environment. One component of the mucus layer is mucin, a complex, disulfide cross-linked polysulfonated glycoprotein matrix. This forms a semi-liquid layer that is a barrier through which molecules must pass in order to gain access to the underlying epithelium. The delivery of pharmaceutically active agents across such a highly charged polysulfonate barrier can be problematic; negatively charged molecules may be repelled by the mucosa while positively charged molecules may be attracted and might be expected to be sequestered via formation of a saturation layer. Thus, the mucus layer lining the mucosal epithelia of the gastrointestinal tract may present a barrier to the effectiveness of bactericidal agents.

In the stomach, bacteria of the species Helicobacter colonize in the mucus layer. Helicobacter within the mucus layer are protected from stomach contents which might otherwise be deleterious to survival of the organism. To eradicate *H.pylori* in the stomach, local acting anti-Helicobacter agents must be able to penetrate or overcome any barrier presented by the mucus. An alternate approach to treating such infections would result in the release of the Helicobacter from the mucus microenvironment by disrupting the mucus with mucolytic agents. Disruption of the mucus would expose the bacteria to contents of the stomach lumen including antimicrobial agents; making the bacteria susceptible to killing by locally acting antimicrobial agents.

Agents known to be active on mucin include lytic enzymes such as glycohydrolases, e.g., α-amylase disclosed in U.S. Pat. No. 5,328,846, or proteinases, e.g., pronase (Kimura et al. Am. J. Gastroenterol. 90: 60–63, 1995), and sulfhydryl compounds, e.g., N-alkyl cysteines, WR2721 and N-(2-mercaptopropionyl)-glycine (MPG). The present invention concerns methods of disrupting the mucus environment of the stomach and exposing the Helicobacter bacteria in the stomach to an efficacious amount of nisin and GML compositions so as to kill the exposed bacteria.

The invention concerns compositions consisting essentially of nisin and GML at concentrations which are suboptimal for the respective agents alone, but which in combination are bactericidal toward the Gram-negative bacteria of the genus Helicobacter and more particularly, the species *Helicobacter pylori*. The nisin and GML compositions are suitable for internal administration to mammals and are effective for eradicating colonization by *H. pylori* and for treatment of infections or other disease states resulting from colonization by *H. pylori*. The invention further provides methods for eradicating colonization of *H. pylori* and for treating infections or other disease states resulting from colonization by *H. pylori,* which comprise administering the novel GML-nisin compositions alone, or in combination with mucolytic agents.

The use of nisin and GML or similar compounds as active substances against a bacterial infection in mammals has advantages from the point of view of ease of delivery of a dosage form and tolerability.

DETAILED DESCRIPTION OF THE INVENTION

Figures 1A, 1B:
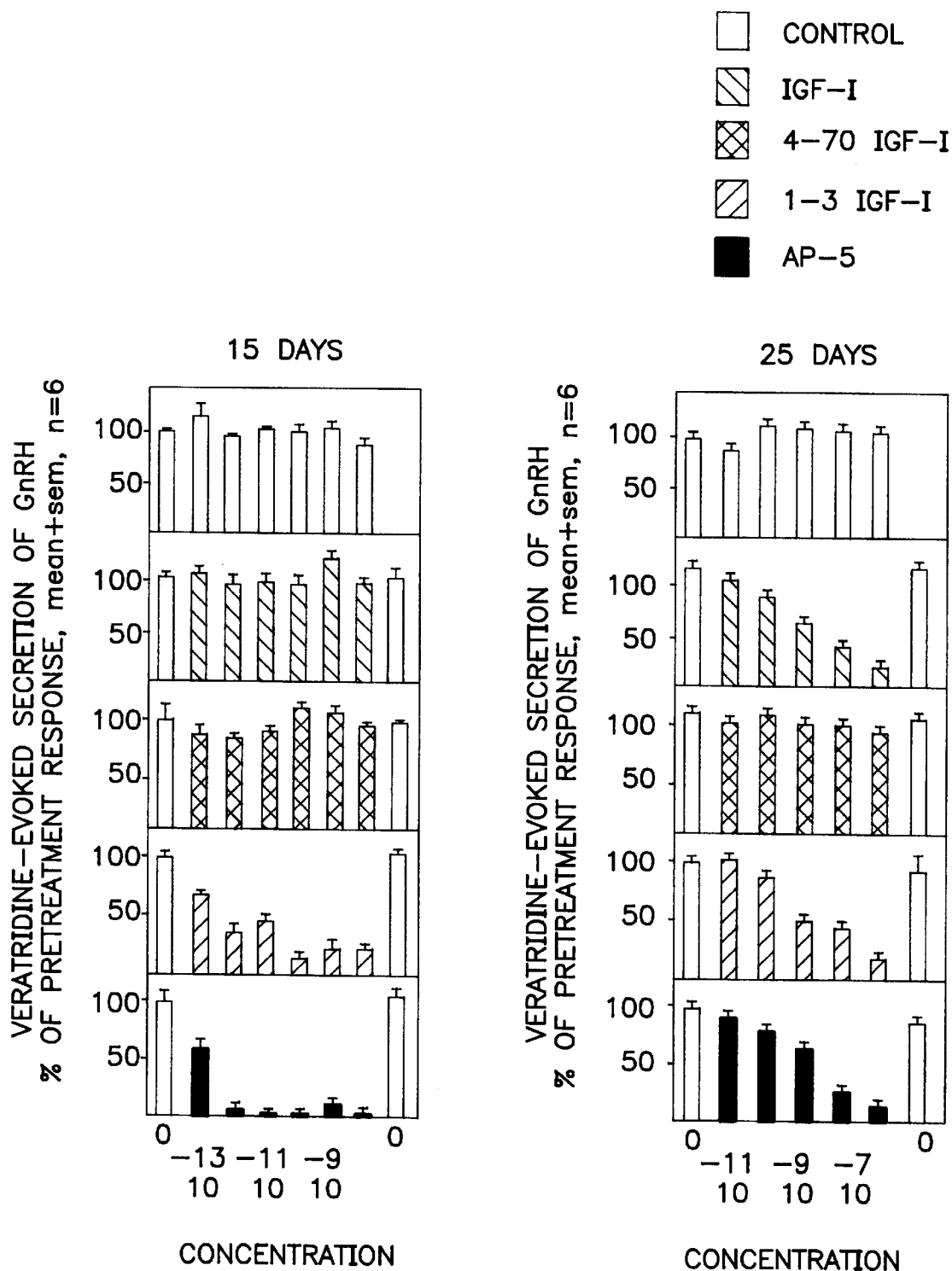

The present invention concerns pharmaceutical compositions and methods of treating infections of the gastrointestinal tract by Gram-negative bacteria of the genus Helicobacter and in particular *H. pylori*. Other bacteria susceptible to the inventive methods of treatment are those of bacterial genera that are very closely related to Helicobacter, such as Campylobacter. Species of Helicobacter include, but are not limited to, *H. pylori* (human), *H. canis* (dog), *H. acinonyx, H. pullorum, H. muridarun, H. cinaedi, H. fennelliae, H. nemestrinae, H. pumetensis, H. bizzozeronii, H. mustelae* (ferret) and *H. felis* (cat). The latter two species of Helicobacter are frequently used in ferret and mouse models of Helicobacter infection. The compositions of the instant invention can also be employed in the killing of *Helico-* bacter pylori colonizing the oral cavity and, thus, in methods for the eradication of bacterial colonization or for the treatment of *H. pylori* infection in the oral cavity.

Nisin concentrations of 30–100 μg/ml or GML concentrations at 10 μg/ml when administered alone and not in combination have little effect on the viability of *H. pylori*. Combinations of 10 μg/ml of GML with 30–100 μg/ml of nisin, however, rapidly produce significant reductions in the viability of this microorganism. The extent of reduction of viability is proportional to the concentration of nisin combined with the GML. The synergistic effect of nisin in combination with GML at concentrations which are suboptimal when they are administered alone was not predictable from the prior art, because it was previously shown that nisin alone at such concentrations was not active against *Helicobacter pylori*.

Other lanthionine bacteriocins with properties similar to nisin may be used. Still further embodiments of the invention concern compositions, and methods of using the compositions, which comprise as active ingredients molecules chemically similar to GML for use in combination with nisin. Such molecules are those derived from glycerol (or other polyhydroxylated compounds, such as sugars) and fatty acids.

For eradication of *H. pylori* colonization or treatment of infections or other disease states resulting from *H. pylori* colonization, the GML and nisin may be administered as separate compositions combined on administration or sequentially administered, or as components of a single formulated composition and may be administered in connection with another pharmaceutically active substance such as a bismuth salt, e.g., bismuth subcitrate or bismuth subsalicylate for treating gastrointestinal disorder. The compositions may be administered in connection with other agents such as cimetidine, ranitidine, omeprazole, lansoprazole, antacids, urease inhibitors or combinations thereof in order to treat some of the diseases and symptoms associated with the presence of *H. pylori* in the gastrointestinal tract. It is contemplated that in these therapies the additional active pharmaceutical agents may be administered concurrently or intermittently with the GML-nisin compositions and the mode of administration may be varied during the course of the treatment as required.

A specific embodiment of the invention concerns methods of treatment which comprise the administration of GML-nisin compositions in tandem with mucolytic agents. Mucolytic agents reduce or eliminate the effects of mucus on the action of the antibacterial agents. The mucus may act to impede the agent from reaching the sites of infection present in the mucosal epithelia. Mucolytic agents decrease the viscosity and disrupt the integrity of the mucus by various mechanisms. Mucolytic sulfhydryl compounds such as N-alkyl-cysteines, Penicillamine, N-(2-mercaptopropionyl)-glycine and WR2721 (the thiophosphate derivative of mercaptoethyl-1,3-diaminopropane) reduce disulfide bridges of the mucin matrix. The mucus may also be disrupted by exposure to hydrolytic enzymes such as glycohydrolases and proteinases, which digest the mucin, and nucleases. In particular, the proteinase, pronase, is useful for disrupting the mucin matrix as disclosed in U.S. Pat. Nos. 4,440,749 and 4,485,095 the contents of which are hereby incorporated by reference.

The performance of the nisin and GML acting locally, either individually or collectively, would potentially benefit from the viscosity of the mucus layer being reduced from normal or from the mucus layer being otherwise disrupted by mucolytic agents. However, the conditions optimal for disruption of the mucus layer by mucolytic agents would frequently be incompatible with the action of certain anti-Helicobacter agents.

In particular, nisin would be inactivated by pronase digestion and would react with sulfhydryl compounds at the neutral or mildly basic pH optima required for these mucolytic agents. On the other hand, if nisin, or other susceptible bactericides in combinations with nisin, were administered in a suitably acidic vehicle so as to reduce the pH in the stomach lumen after the mucolytic agents have acted, the activity of the sulfhydryl groups in the one instance, and the activity of the enzymes in the other, would be inhibited or inactivated in the stomach by the low pH and by reactivation of stomach pepsin. Those bactericidal agents and their combinations which are not inactivated or inhibited by acid or pepsin would now act more efficiently against Helicobacter to effect a more efficient cure of the Helicobacter infection. Indeed, disruption of the bacteria's microenvironment and exposure to acidic pH would of itself be, in part, detrimental to survival of the acid-sensitive Helicobacter, further contributing to the performance of the bactericidal agents.

Moreover, the use of pronase as disclosed by Kimura et al., requires that the antibiotics used in that instance be removed from the stomach by a nasogastric tube in order to prevent their going on to produce side effects. Embodiments of the invention comprising the use of acid-stable bactericides that are subsequently eliminated from the intestine by absorption as in the case of monoglycerides, or destroyed by pancreatic enzymes as in the case of nisin would not require removal of the bactericides from the stomach other than by normal stomach emptying. This would be a significant advantage because it eliminates the need to remove the anti-Helicobacter agents from the stomach by a nasogastric tube, an unpleasant, expensive, and potentially unacceptable procedure for some patients.

Mucolytic sulfhydryl compounds optimally reduce disulfides at pH values of 7.0 or higher. A neutral to basic stomach environment can be provided by co-administering a sulfhydryl compound with a suitable buffer such as bicarbonate or by co-administration with a gastric acid inhibitor. Since few mucolytic enzymes are capable of acting or surviving in the harsh acidic environment of the stomach, where they are susceptible to digestion in acid by stomach pepsin, they also must be administered with an agent which raises the pH of the stomach contents. Therefore, in treating *H.pylori* with a proteinase such as pronase, an antisecretory agent, such as an $H_2$-antagonist or proton pump inhibitor may be co-administered to inhibit acid secretion so that the proteinase is delivered in a neutral or mildly basic environment. Alternatively, or in connection with such treatment, the proteinase may be delivered in a mildly basic buffer, such as bicarbonate, to neutralize gastric acid. Also as an alternative, the pH-raising buffer or the antisecretory agent may be administered separately prior to administration of the mucolytic agent.

Because nisin is a sulfhydryl-containing polypeptide, mucolytic agents which are sulfhydryl compounds or proteinases should be administered prior to, and not simultaneously with, the nisin-GML composition.

In another embodiment of the invention, the therapy combining GML-nisin treatment and treatment with a mucolytic agent may be expanded to include treatment with other bactericidal agents. Bactericides which act rapidly and locally in the stomach to kill Helicobacter would be expected to have fewer side effects than those associated with agents such as antibiotics that are absorbed into the systemic circulation, or that pass into the intestine. Such antibiotics may adversely affect the normal intestinal microflora, thereby, enabling opportunistic pathogens to colonize the intestine. Thus, co-administration with antibiotics is preferably not undertaken unless it is the most effective means of eliminating the infection under the circumstances.

The typical daily doses of the active components of the compositions may vary according to the infection being treated, the site of infection and the symptoms of the disease being treated. The effective oral dosage of the nisin component is in the range from 0.5 mg to 5000 mg, and the effective oral dosage of the GML component is in the range from 0.1 mg to 2000 mg. The preferred dosage ranges for nisin and GML, respectively, are from 10 mg to 2000 mg and from 10 mg to 1000 mg.

Mucolytic agents such as pronase can be administered in a dosage range from 18,000 –36,000 tyrosine units for a single administration as disclosed in Kimura et al., *Am. J. Gastroenterol.* 90: 60–63, 1995, the disclosure of which is hereby incorporated by reference in its entirety. N-alkylcysteines can be administered in a dosage range from 0.1 to 1.0 g for a single administration.

The methods of the invention for eradicating colonization and treating infection by bacteria of the genus Helicobacter comprise administering an effective amount of a GML-nisin composition to a patient in need of such treatment. In one embodiment, the method comprises administering the GML-nisin composition 1–4 hours following treatment with a mucolytic agent; the mucolytic agent is administered in combination with an antacid or a slightly basic buffer such as bicarbonate. In another embodiment, the method utilizing a hydrolytic enzyme or a sulfhydryl compound as the mucolytic agent comprises pretreating the patient with an inhibitor of gastric acid secretion or a basic buffer to raise the pH of the stomach contents before the administration of the mucolytic agent; administration of the latter precedes the administration of the nisin-GML composition.

EXAMPLE 1

Synergistic Bactericidal Activity of Nisin and GML, in the Absence of chelators, against *H. pylori*

All tests of bactericidal activity in this example were conducted for 30 minutes at 37° C. The parameter measured was survival of bacteria exposed to GML and/or nisin, as determined by viable counts (colony forming units per ml [CFU/ml]) determined by standard dilution and plating techniques. Media, growth and test conditions were as follows: All cultures of Helicobacter were incubated under microaerobic conditions in GasPak. *H. pylori* was cultured for 2 to 4 days on Trypticase Soy agar+5% defibrinated sheep blood and then inoculated into NYCIII broth and grown overnight with gentle shaking. [NYCIII broth contains, per liter: 1 g soluble starch (Difco), 15 g proteose peptone #3 (Difco), 5 g NaCl, 4 g$K_2HPO_4$, 1 g $KH_2PO_4$, 5 g glucose, 25 ml fresh yeast extract (Gibco), 120 ml gamma-globulin-free horse serum (Sigma)]. Suspensions for testing the activity of GML and nisin were in 10% sucrose. Viable counts were determined after 3–5 days' growth on Trypticase Soy agar-5% sheep blood.

Figure 1:
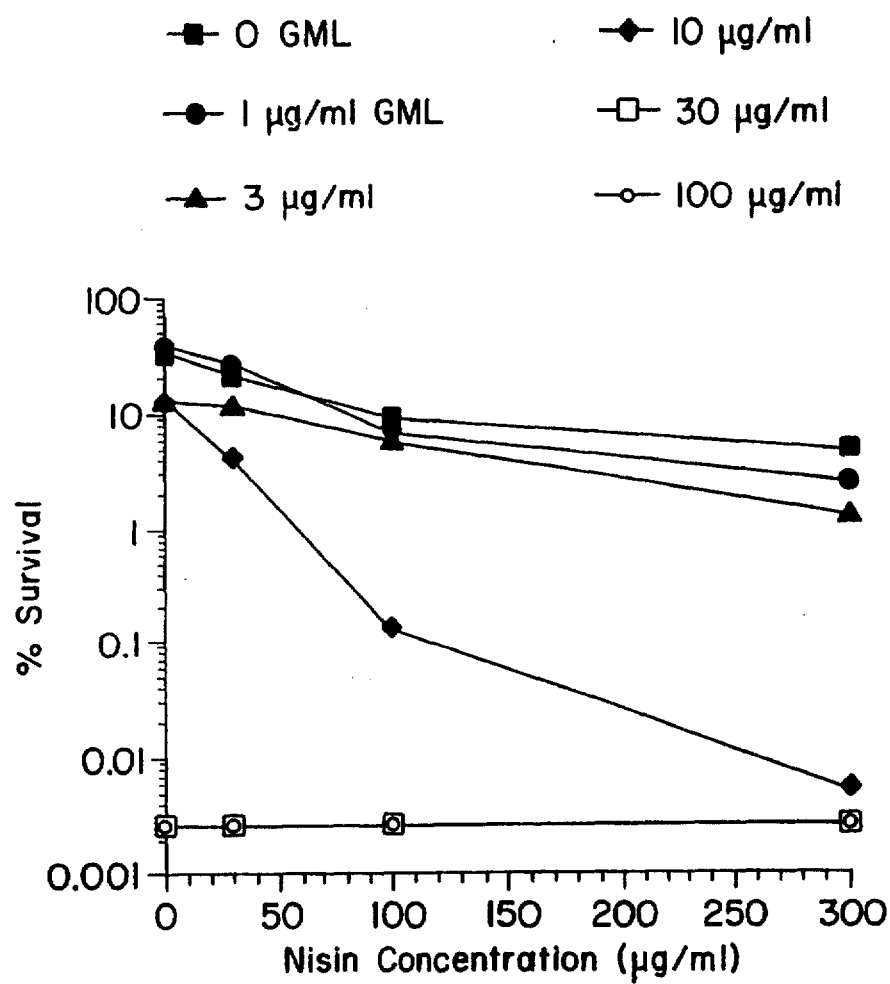

FIG. 1 shows the effect of combining different concentrations of GML with different concentrations of nisin on the viability of *H. pylori* strain ATCC 43504. A suspension of bacteria was divided and exposed to different concentrations of the agents, singly or combined. Survival of bacteria is expressed relative to the unincubated (zero time) control suspension. Nisin alone, at concentrations between 30 and 300 μg/ml, had little or no effect on the viability of *H. pylori* (survival ≥10%). At concentrations of 1 and 3 μg/ml GML, in the absence of nisin, there was also little or no reduction in the viability of the inoculum (survival≥10%). When exposed to these concentrations of GML plus 300 μg/ml of nisin, a very slight further drop in the viability of the cultures was observed. When the bacteria were exposed to 10 μg/ml of GML alone, again more than 10% of the bacteria survived. However, the addition of increasing amounts of nisin (30, 100 or 300 μg/ml) to the 10 μg/ml of GML produced highly significant drops in the viability of the culture; the extent of this effect increased with increasing concentration of nisin. Higher concentrations of GML alone (30 or 100 μg/ml) sterilized the bacterial suspensions.

The GML-nisin-containing compositions of the invention are preferably administered orally in the form of preparations which contain an effective amount of both active agents and a pharmaceutically acceptable carrier. A pharmaceutical mucolytic preparation comprising an effective amount of a mucolytic agent and a pharmaceutically acceptable carrier may be administered prior to the GML-nisin-containing preparation.

The compositions of the invention may also be formulated as antacid compositions, or administered in combination with an antacid wherein the administration would result, for instance, in a higher stomach pH environment than that existing prior to administration. The GML-nisin compositions would still be effective against the pathogenic bacteria under such conditions.

The GML-nisin-containing preparations further comprising an antacid may also be administered subsequent to a pharmaceutical mucolytic preparation comprising an effective amount of a mucolytic and a pharmaceutically acceptable carrier.

The pharmaceutically acceptable carrier may be in the form of a solid, semi-solid or liquid diluent. Pharmaceutically acceptable carriers may include cellulose derivatives, gelatin, lactose, starch, etc. The preparations may be in the form of solutions, colloids or emulsions, powders, tablets, capsules or gels.

The dry forms of the preparations may be pressed into tablets which may be coated with a pharmaceutically inert ingredients such as sugar, and which may contain other pharmaceutically acceptable substituents such as gum arabic, gelatin, talc, or titanium dioxide and may be also coated with various dyes. Hard gelatin capsules may be prepared which contain granules of the active agents in combination with a solid carrier such as lactose, potato starch, corn starch, cellulose derivatives or gelatin.

Liquid preparations for oral administration may be prepared in the form of syrups or suspensions comprising the GML- nisin-containing composition plus sugar, water and glycerol or propylene glycol. If desired, such liquid preparations may contain coloring agents, flavoring agents, sweeteners such as saccharin and thickening agents such as cellulose derivatives.

Delivery of a dosage could obviously be achieved by modifications of the simple aqueous formulations by inclusion of thickeners, emulsifiers, or particulates to effect a colloidal suspension. The use of emulsifiers such as lecithin would be of particular use in forming stable emulsions more suitable for delivery to the area of colonization.

We claim:

1. A composition consisting essentially of an effective amount of GML, an effective amount of nisin in the absence of chelator and a pharmaceutically acceptable carrier.

2. A method for eradicating colonization or treating infections or other disease states resulting from colonization by bacteria of the genus Helicobacter in the gastrointestinal tract of a mammal, which comprises administering to a mammal in need of such treatment an effective amount of a GML-nisin composition.

3. A method for eradicating colonization or treating infections or other disease states resulting from colonization by bacteria of the genus Helicobacter in the oral cavity of a mammal, which comprises administering to a mammal in need of such treatment an effective amount of a GML-nisin composition.

4. A method according to claim 2 or 3, wherein GML is administered in a dosage range from 0.1 mg to 2000 mg, and nisin is administered in a dosage range from 0.5 mg to 5000 mg.

5. A method according to claim 4, wherein GML is administered in a dosage range from 10 mg to 1000 mg, and nisin is administered in a dosage range from 10 mg to 2000 mg.

6. The method according to claim 2, whereby administration of the GML-nisin composition is preceded by administering to the mammal an effective amount of a mucolytic agent.

7. The method according to claim 6, wherein the mucolytic agent is a sulfhydryl compound.

8. The method according to claim 6, wherein the mucolytic agent is a hydrolytic enzyme.

9. The method according to claim 8, wherein the enzyme is pronase.

10. The method according to claim 6, wherein the mucolytic agent is administered in combination with an amount of an antacid or a buffer effective to raise the pH at the site of administration to 7 or higher.

11. The method according to claim 6, wherein administration of the mucolytic agent is preceded by administration of an amount of an antacid or a buffer effective to raise the pH at the site of administration to 7 or higher.

* * * * *

UNITED STATES PATENT AND TRADEMARK OFFICE
CERTIFICATE OF CORRECTION

PATENT NO. : 5,804,549
DATED : September 8, 1998
INVENTOR(S) : Peter Blackburn et al.

It is certified that error appears in the above-identified patent and that said Letters Patent is hereby corrected as shown below:

Delete Figs. 1A and 1B and substitute therefore Fig. 1, as shown on attached page.

Signed and Sealed this

Fifth Day of March, 2002

*Attest:*

*Attesting Officer*

JAMES E. ROGAN
*Director of the United States Patent and Trademark Office*